United States Patent
Pöchlauer et al.

(10) Patent No.: US 6,225,095 B1
(45) Date of Patent: May 1, 2001

(54) ENZYMATIC PROCESS FOR THE PREPARATION OF (S)-CYANOHYDRINS

(75) Inventors: Peter Pöchlauer, Linz; Michael Schmidt, St. Oswald; Irma Wirth, Enns; Rudolf Neuhofer, Mittertreffling; Antonia Zabelinskaja-Mackova; Herfried Griengl, both of Graz; Cor Van den Broek, Landgraaf; Raf Reintjens, Etten-Leur; Herman Jelle Wories, Maastricht, all of (NL)

(73) Assignee: DSM Fine Chemicals Austria GmbH, Linz (AT)

( * ) Notice: Subject to any disclaimer, the term of this patent is extended or adjusted under 35 U.S.C. 154(b) by 0 days.

(21) Appl. No.: 09/222,344

(22) Filed: Dec. 29, 1998

(30) Foreign Application Priority Data

Dec. 29, 1997 (AT) .................................................. 2192/97

(51) Int. Cl.$^7$ ................................ C12P 13/00; C12N 9/88
(52) U.S. Cl. ........................................... 435/128; 435/232
(58) Field of Search ....................... 435/128, 232

(56) References Cited

U.S. PATENT DOCUMENTS

| 5,346,816 | 9/1994 | Griengl et al. ........................ 435/128 |
| 5,350,871 | * 9/1994 | Geluk et al. ........................... 558/351 |

OTHER PUBLICATIONS

Wajan, H. et al., J. Biol. Chem., vol. 271, No. 42, pp. 25830–25834, Oct. 1996.*

* cited by examiner

Primary Examiner—Ponnathapu Achutamurthy
Assistant Examiner—Peter P. Tung
(74) Attorney, Agent, or Firm—Wenderoth, Lind & Ponack, L.L.P.

(57) ABSTRACT

Process for the preparation of the (S)-enantiomers of optically active cyanohydrins, in which a reaction mixture of a) an aldehyde or ketone dissolved in an organic, water-immiscible or slightly miscible diluent, b) an aqueous (S)-hydroxynitrile lyase solution and c) a cyanide group donor is stirred in such a way that an emulsion is formed which is maintained up to the end of the reaction by stirring.

8 Claims, No Drawings

ENZYMATIC PROCESS FOR THE PREPARATION OF (S)-CYANOHYDRINS

Cyanohydrins are of importance, for example, for the synthesis of alpha-hydroxy acids, alpha-hydroxy ketones, and beta-aminoalcohols, which are used for obtaining biologically active substances, e.g. pharmaceutical active compounds, vitamins or alternatively pyrethroid compounds.

The preparation of a cyanohydrin can be carried out by addition of hydrocyanic acid (HCN) to the carbonyl group of an aldehyde or of an unsymmetrical ketone, enantiomer mixtures of unsymmetrical cyanohydrins resulting.

Since normally only one of the two enantiomers in a biologically active enantiomer mixture is biologically active, there has not been a lack of attempts to find a process for the preparation of the (S)-enantiomer of an optically active cyanohydrin in as high as possible optical purity.

Thus, for example, in Makromol. Chem. 186, (1985), 1755–62 a process for obtaining (S)-cyanohydrins by reaction of aldehydes with hydrocyanic acid in the presence of benzyloxycarbonyl-(R)-phenylalanine-(R) histidine methyl ester as a catalyst is described. The optical purity of the (S)-cyanohydrins obtained, however, is extremely unsatisfactory.

EP-A-0 326 063 describes an enzymatic process for the preparation of optically active (R)- or (S)-cyanohydrins by reaction of aliphatic, aromatic or heteroaromatic aldehydes or ketones with hydrocyanic acid in the presence of (R)-oxynitrilase (EC 4.1.2.10) from *Prunus amygdalis* or oxynitrilase (EC 4.1.2.11) from Sorghum bicolor. Examples of the stereospecific preparation of aliphatic (S)-cyanohydrins are not indicated. This is not surprising, since in Angew. Chemie 102 (1990), No. 4, pp 423–425 it is stated by inventors who are mentioned in EP-A-0 326 063 that no aliphatic (S)-cyanohydrins can be prepared using hydrocyanic acid in the presence of the (S)-oxynitrilase from Sorghum bicolor. This finding is also confirmed by F. Effenberger et al. in Tetrahedron Letters Vol. 31 No. 9 (1990), pp. 1249–1252.

EP 0 632 130 further describes a process in which aliphatic aldehydes or unsymmetrical aliphatic ketones are reacted stereospecifically with hydrocyanic acid and oxynitrilase from *Hevea brasiliensis* to give (S)-cyanohydrins. The reaction is carried out according to EP 0 632 130, preferably in an aqueous diluent without addition of organic solvents, since these, as described in EP 0 632 130, rapidly inhibit the activity of the enzyme.

The processes known up to now were mostly carried out under rather dilute conditions, either in an aqueous or organic system or in a two-phase system. This procedure, however, has disadvantages for many starting materials. Thus, for example, 3-phenoxybenzaldehyde or 4-fluoro-3-phenoxybenzaldehyde or various ketones are poor substrates, so that a high use of enzyme is necessary in order to obtain an acceptable yield of cyanohydrins in good optical purity.

It has now unexpectedly been found that the reaction of a large number of carbonyl compounds, such as, for example, aliphatic, alicyclic, unsaturated, aromatically substituted aliphatic, aromatic, and also heteroaromatic aldehydes and ketones, to give the corresponding cyanohydrins in high yield and high optical purity is possible in a process which is more concentrated in relation to the prior art and with lower use of enzyme if the reaction is carried out in an emulsion. Unexpectedly, the enzyme activity under the conditions of an emulsion such as, for example, high stirring energy, which in the case of many proteins lead to deactivation, remains stable.

The present application therefore relates to a process for the preparation of the (S)-enantiomers of optically active cyanohydrins by reaction of an aldehyde or of a ketone with a cyanide group donor in the presence of a native or of a recombinant (S)-hydroxynitrile lyase, which comprises stirring a reaction mixture of a) an aldehyde or ketone dissolved in an organic water-immiscible or slightly miscible diluent, b) an aqueous (S)-hydroxynitrile lyase solution and c) a cyanide group donor in such a way that an emulsion is formed, which is maintained up to the end of the reaction by stirring, after which the corresponding (S)-cyanohydrin is isolated from the reaction mixture by phase separation after reaction is complete The starting materials employed in the process according to the invention are an aldehyde or a ketone, a cyanide group donor, an aqueous solution of a native or recombinant hydroxynitrile lyase (Hnl) and an organic diluent which is immiscible or slightly miscible with water.

Aldehydes in this case are understood as meaning aliphatic, aromatic or heteroaromatic aldehydes. Aliphatic aldehydes in this case are understood as meaning saturated or unsaturated aliphatic, straight-chain, branched or cyclic aldehydes. Preferred aliphatic aldehydes are straight-chain aldehydes, in particular having 2 to 18 C atoms, preferably from 2 to 12, which are saturated or mono- or polyunsaturated. The aldehyde can in this case have both C—C double bonds and C—C triple bonds. The aldehyde can be unsubstituted or substituted by groups which are inert under the reaction conditions, for example by optionally substituted aryl or heteroaryl groups such as phenyl or indolyl groups, or by halogen, ether, alcohol, acyl, carboxylic acid, carboxylic acid ester, nitro or azido groups.

Examples of aromatic or heteroaromatic aldehydes are benzaldehyde and variously substituted benzaldehydes such as, for example, 3,4-difluorobenzaldehyde, 3-phenoxybenzaldehyde, 4-fluoro-3-phenoxybenzaldehyde, and further furfural, anthracene-9-carbaldehyde, furan-3-carbaldehyde, indole-3-carbaldehyde, naphthalene-1-carbaldehyde, phthalaldehyde, pyrazole-3-carbaldehyde, pyrrole-2-carbaldehyde, thiophene-2-carbaldehyde, isophthalaldehyde or pyridine aldehydes etc.

Ketones are aliphatic, aromatic or heteroaromatic ketones in which the carbonyl carbon atom is unequally substituted. Aliphatic ketones are understood as meaning saturated or unsaturated, straight-chain, branched or cyclic ketones. The ketones can be saturated or mono- or polyunsaturated. They can be unsubstituted, or substituted by groups which are inert under the reaction conditions, for example by optionally substituted aryl or heteroaryl groups such as phenyl or indolyl groups, or by halogen, ether, alcohol, acyl, carboxylic acid, carboxylic acid ester, nitro or azido groups.

Examples of aromatic or heteroaromatic ketones are acetophenone, indolylacetone etc.

Aldehydes and ketones which are suitable for the process according to the invention are known or can be prepared in the customary manner.

Hydrocyanic acid is added as a cyanide group donor. The hydrocyanic acid can in this case also be released from one of its salts such as, for example, NaCN or KCN only shortly before the reaction and added to the reaction mixture in undiluted form or in dissolved form.

As a hydroxynitrile lyase (Hnl), native (S)-hydroxynitrile lyases, e.g. from cassava and *Hevea brasiliensis*, and also recombinant (S)-Hnl. Preferably, the native Hnl used is Hnl from *Hevea brasiliensis* or *Manihot esculenta*. Suitable recombinant (S)-Hnl is obtained, for example, from genetically modified microorganisms such as, for example, *Pichia pastoris* or *Saccharomyces cerevisiae*.

Preferably, recombinant (S)-Hnl from *Pichia pastoris* is employed.

As a result of the functional overexpression in the methylotrophic yeast *Pichia pastoris,* this Hnl can be obtained in any desired amount (M. Hasslacher et al., J. Biol. Chem. 1996, 271, 5884). This expression system is particularly suitable for fermentations at a high cell density. Thus it is possible to obtain approximately 20 g of pure enzyme per liter of fermentation medium. The specific activities of the purified recombinant protein achievable are approximately twice as high as those of the natural enzyme, which was isolated from the leaves of the tree *Hevea brasiliensis*. After cell destruction, the cytosolic fraction can be used without further purification, whereby the expenditure of labor is minimized. The enzyme is not glycosylated and also has no prosthetic group which would lead to inactivation on removal of the protein moiety.

The Hnl can be employed at room temperature for several days without significant loss of activity, and is adequately stable long-term at −20° C. As a result, the possibility of the repeated use of the same enzyme batch results. The enzyme is also distinguished by a high stability to solvents. The possibility therefore exists of employing various organic solvents, which allow the formation of an emulsion, for the enzymatic reaction, which has a favorable effect on the productivity of the respective process.

The hydroxynitrile lyase can be employed in purified or unpurified form, as such or immobilized. The hydroxynitrile lyase can be prepared and purified, for example, by precipitation with ammonium sulfate and subsequent gel filtration, for example according to Selmar et al., Physiologia Plantarum 75 (1989), 97–101.

Organic diluents which can be used are aliphatic or aromatic hydrocarbons which are immiscible or slightly miscible with water and which are optionally halogenated, alcohols, ethers or esters or mixtures thereof.

Preferably, methyl tert-butyl ether (MTBE), diisopropyl ether, dibutyl ether and ethyl acetate or a mixture of MTBE and toluene are employed.

Per g of aldehyde or ketone, approximately 0.1 to 10 g of diluent and 10 to 10,000 IU of hydroxynitrile activity lyase, preferably approximately 50 to 2000 IU, are added.

An IU (International Unit) designates that amount of an enzyme preparation which catalyzes the formation of one micromole of product per minute. The amount of the respective hydroxynitrile lyase needed is best determined in an activity test, for example according to Selmar et al., Analytical Biochemistry 166 (1987), 208–211.

Per mole of aldehyde or keto group employed, at least 1 mol, preferably 1 to 5 mol, particularly preferably 1 to 2 mol, of cyanide group donor are added.

In the process according to the invention, the aldehyde or the ketone is present dissolved in the organic diluent. The enzyme is added to this solution in the form of an aqueous buffer solution. The pH of this solution should be below 7, preferably between 3 and 6.5.

The reaction mixture thus obtained is stirred at temperatures from 0° to approximately 30° C. such that an emulsion results. The stirrer speed (N) necessary for this in this case depends on the so-called power characteristic of the stirrer employed (Po), its diameter (d), the reaction volume (V) and the density (p) of the reaction medium. The stirring energy, i.e. the stirrer power per reaction volume (volume of the reaction mixture, not of the apparatus) can be derived from these factors.

$$P/V = \frac{P_0 \cdot \rho \cdot N^3 \cdot d^3}{V}$$

Preferably, the stirring energy in the process according to the invention is over 500 W/m$^3$, particularly preferably over 1000 W/m$^3$. Comparatively, in processes known up to now, which operate, for example, in aqueous, organic or two-phase systems, stirring energies of only approximately 100 W/m$^3$ have been achieved.

If the reaction mixture is present as an emulsion, the cyanide group donor is added. The emulsion is maintained up to the end of the reaction by stirring. The course of the reaction can in this case be monitored photometrically by means of the decrease in the aldehyde content.

Depending on the starting material, measurement is carried out at the wavelength at which the starting material absorbs and the resulting cyanohydrin does not. The absorption of the reaction mixture thus decreases proportionally with increasing conversion.

When using a salt of hydrocyanic acid, the hydrocyanic acid can first be liberated from a solution of the salt by addition of, for example, $H_2SO_4$ or $H_3PO_4$.

The pH of this solution of hydrocyanic acid should be under 7, preferably between 4 and 6.5.

The aqueous enzyme solution, the organic diluent and the aldehyde or the ketone are then added to the hydrocyanic acid solution, the reaction is started and, if necessary, the pH is readjusted.

Here too, care is to be taken that the reaction mixture is stirred in such a way that an emulsion results, which in turn is maintained up to the end of the reaction by continuous stirring.

For the working-up of the reaction mixture and for the isolation of the cyanohydrin formed, customary techniques which first break the emulsion, such as, for example, filtration, centrifugation or coalescence, are employed. The phases formed are then separated, if necessary with addition of demulsifiers, and the product-containing phase is worked up.

To obtain the corresponding cyanohydrin, depending on the final product, known techniques such as distillation, extraction or crystallization are used here. The cyanohydrins thus obtained can optionally be stabilized by addition of an acid before further processing.

EXAMPLES 1–8

Preparation of (S) -3 -phenoxybenzaldehyde cyanohydrin

Example 1 a) 15 g (0.0756 mol) of m-phenoxybenzaldehyde were dissolved in 45 ml of MTBE, introduced into a 150 ml double-jacket vessel having a 6-blade stirrer and the reaction mixture was brought to 15° C.

26.4 ml of enzyme (Hnl from *Pichia pastoris,* supernatant of the centrifugation of the undiluted cell lysate) were mixed into a solution of 1.5 g of sorbitol in 33.6 ml of demineralized water (pH 5.8), adjusted to pH 5.5 using dilute citric acid solution and introduced into the reactor. 3×5 ml of HCN were then added via a syringe with a 3-way tap. The reaction solution was already being stirred at 600 rpm during the course of this.

During the reaction, it was stirred at 800 rpm so that the reaction mixture was present in the form of an emulsion. The course of the reaction was monitored by means of IP checking via the decrease in the aldehyde content (extinction at 304 nm). To this end, 0.5 to 1 ml of reaction solution were removed and centrifuged after defined reaction times. 100 μl of organic phase were diluted to 10 ml with MTBE, 250 μl of which were in turn diluted to 10 ml with MTBE such that the total dilution corresponded to a factor of 100×40=4000. Toward the end of the reaction (conversion >95%), the extinction became very small, such that to increase the accuracy the 2nd dilution step was dispensed with; the extinction in this case was divided by the 2nd dilution factor (40) before calculation of the conversion.

$$\text{Conversion}(t) = [1 - (\text{extinction }(t)/\text{extinction }(\text{start}))] \times 100\%$$

The following conversions were calculated:

| Reaction time | Conversion | |
|---|---|---|
| 0 | 0 | |
| 30 | 70 | |
| 60 | 85 | |
| 90 | 95 | |
| 120 | 95 ... | extinction already very small, reaction stops |

(conductivity at the end of the reaction 0.8 mS)

b) The above set of reactions was repeated, but stirring was carried out at 1000 rpm.

| Reaction time | Conversion | |
|---|---|---|
| 0 | 0 | |
| 60 | 90 | |
| 90 | >95 | |
| 120 | >95 ... | extinction already very small, according to thin-layer chromatography (TLC) reaction takes place up to a conversion of 98% |

(conductivity at the end of the reaction 0.7 mS)

c) For comparison, the above batch was repeated a further time, but it was only stirred at 400 rpm.

| Reaction time | Conversion |
|---|---|
| 0 | 0 |
| 30 | 30 |
| 60 | 70 |
| 90 | 75 |

(conductivity at the end of the reaction 0.8 mS)

The stirring energy of the 3 batches was determined according to the following formula:

$$P/V = \frac{P_0 \cdot \rho \cdot N^3 \cdot d^3}{V}$$

$P_0$ power characteristic of the stirrer
$\rho$ density [kg/m$^3$]
N stirrer speed [rpm]
d stirrer diameter [m]
V reaction volume [m$^3$]

| Example 1 | rpm | Stirring energy [W/m$^3$] | |
|---|---|---|---|
| a | 800 | 588 | $P_0$ ... 3 |
| b | 1000 | 1146 | d ... 0.5 |
| c | 400 | 73 | V ... 134 ml |

Example 2

Analogously to Example 1, 75 g (0.378 mol) of m-phenoxybenzaldehyde in 225 ml of MTBE and 132 ml of enzyme solution were reacted with 73. ml (1.89 mol) of HCN in a 750 ml double-jacket vessel with a 6-blade stirrer.

In order to obtain an emulsion, stirring was carried out here at 770 rpm, which corresponded to a stirring energy of about 1150 W/m$^3$.

| Reaction time | Extinction | Conversion |
|---|---|---|
| 0 | | 0 |
| 30 | 0.499 | 80 |
| 60 | 0.1 | >95 |
| 90 | | >98 |

Reaction complete after 1.5 h.

Working-up:

150 ml of the reaction mixture were shaken with 75 ml of MTBE and passed through a column packed with glass wool (height 9 cm, diameter 3 cm) at low pressure. The run-off consisted of a clear organic and a yellow, slightly cloudy aqueous phase. A further 300 ml of undiluted reaction mixture were then passed through the same column, a clean phase separation likewise being obtained. Small amounts of solid concentrated in the column and were removed with water and MTBE. It was then possible to use the column again for the phase separation.

The MTBE phases were collected and concentrated in a rotary evaporator:

Residue: (S)-3-phenoxybenzaldehyde cyanohydrin (SCMB) 52.7 g (92%)

Example 3

13.8 g (0.28 mol) of NaCN were dissolved in 12 ml of demineralized water, introduced into a round-bottomed flask and rinsed in with water (to 90 ml) 10% H$_2$SO$_4$ was added with ice-cooling from a dropping funnel such that a pH of 5.6 was achieved. The mixture thus obtained was introduced into a 750 ml double-jacket vessel having a 6-blade stirrer. 26.4 ml of enzyme (Hnl from *Pichia pastoris* supernatant of the centrifugation of the undiluted cell lysate, 850 IU/ml) were diluted to 130 ml with water and likewise introduced into the reactor. The pH of the reaction mixture was readjusted to 5.5, 180 ml of MTBE and 31 g (0.156 mol) of m-phenoxybenzaldehyde were added and the reaction was started. Stirring was carried out here at 500 rpm (3.8 kW/m$^3$), an emulsion resulting. The course of the reaction was again monitored photometrically.

| Reaction time | Extinction | Conversion |
| --- | --- | --- |
| 0 | | |
| 60 | 0.129 | about 70 |
| 120 | 0.079 | about 85 |
| 180 | 0.060 | about 90 |

Example 4

Analogously to Example 3, 6 9 g (0.141 mol) of NaCN, 15.5 g (0.0781 mol) of m-phenoxybenzaldehyde, 26.4 ml of enzyme (850 IU/ml) in 45 ml of MTBE and 16.1 ml of water were reacted at pH 5.6 (adjusted using 10% strength $H_2SO_4$) in a 150 ml double jacket vessel having a 6-blade stirrer. The reaction mixture was stirred such that an emulsion resulted.

The stirrer speed was initially 1000 rpm. It was calculated from the stirrer dimensions that the nominal power of the reaction unit is only reached at 1860 rpm, so the speed was increased to this value after 2.5 h.

| Reaction time | Extinction | Conversion |
| --- | --- | --- |
| 0 | | |
| 60 | 0.49 | |
| 120 | 0.36 | 60–65 |
| 180 | 0.20 | about 80 |
| 240 | 0.07 | about 90–95 |

As a result of the increase in the stirrer speed after 150 min, the reaction was markedly accelerated.

Example 5

Analogously to Example 4, 13.8 g (0.28 mol) of NaCN, 31 g of m-phenoxybenzaldehyde, 26.4 ml of enzyme in 45 ml of MTBE and 220 ml of water were reacted at pH 5.6 (adjusted using 10% strength $H_2SO_4$) at 15° C. in a 750 ml double-jacket vessel having a 6-blade stirrer. Again, the mixture was stirred so rapidly that an emulsion resulted. The stirrer speed was 500 rpm (5.1 kW/m$^3$, corrected to actual reaction volume).

| Reaction time | Extinction | Conversion |
| --- | --- | --- |
| 0 | | |
| 90 | 0.20 | about 70 |
| 165 | 0.047 | about 90 |
| 210 | 0.041 | about 95 |

Working-up was carried out by passing through a glass column.

The product was obtained pure by distilling off the solvent. An analytical sample was withdrawn and acetylated in the customary manner by reaction with acetyl chloride in dichloromethane and its residual aldehyde content and its enantiomeric excess (ee) were determined by chromatography on a chiral gas chromatography column:

GC analysis: Conversion 97% e.e. 98%

Example 6

88 ml of enzyme (850 U/ml) were mixed with 112 ml of water, adjusted to pH 5.5 by means of 0.1% strength citric acid and introduced into a 750 ml double-jacket vessel having a 6-blade stirrer. 50 g (0.252 mol) of m-phenoxybenzaldehyde were dissolved in 150 ml of MTBE and added to the enzyme solution. The reaction mixture was brought to 15° C. and stirred at 500 rpm (6 kW/m$^3$) such than an emulsion was present. 12.3 g (0.454 mol) of HCN were then added via a dropping funnel in the course of 30 min. The course of the reaction was again monitored photometrically.

| Reaction time | Extinction | Conversion |
| --- | --- | --- |
| 0 | | |
| 30 | 0.795 | about 30 (end of the dropwise addition) |
| 90 | 0.227 | about 75 |
| 150 | 0.079 | about 92 |
| 180 | 0.057 | about 95 |
| 240 | | about 98 (TLC) |

The reaction mixture was worked up by phase separation on a column packed with glass wool.

GC analysis: Conversion 98% e.e. 99%

Example 7

4 g of native (S)-hydroxynitrile lyase (Hnl) from Hevea brasiliensis were suspended in 100 ml of Na citrate buffer (5 mmol), stirred at room temperature for 2.5 h and centrifuged and the supernatant was concentrated to 10 ml on a Rotavapor (30° C., 1 mbar). After measurement of the activity (348 IU/g), the enzyme was transferred to a 25 ml round-bottomed flask, and 1 g (5 mmol) of m-phenoxybenzaldehyde and 1.5 ml of tert-butyl methyl ether (MTBE) were added.

The reaction mixture thus obtained was then stirred at 0–5° C. with a stirring energy of approximately 1 kW/m$^3$ (magnetic stirrer) until an emulsion resulted. 0.3 ml of HCN (7.7 mmol) was then rapidly added dropwise and stirring was continued for 23 h at 0–5° C. with undiminished stirring energy.

The course of the reaction was monitored by means of IP checking via decrease in the m-phenoxybenzaldehyde content (photometric measurement at 304 nm).

The reaction solution was centrifuged after reaction was complete, the enzyme was removed and the residual solution was diluted with 2.5 ml of MTBE, shaken and centrifuged again.

(S)-3-Phenoxybenzaldehyde cyanohydrin remained as a residue in the organic phase. (e.e.=90.6%, purity 91.4%) (determined by gas chromatography) The conversion was 92.7% after 23 h.

Comparison experiment

Analogously to Tetrahedron, Vol. 52, No. 23, pp 7833–7840, (S)-3-phenoxybenzaldehyde was prepared by reaction of m-phenoxybenzaldehyde with KCN in an aqueous citric acid buffer (pH=4.0–4.5) (HCN is formed in situ) using Hnl from *Pichia pastoris*. The stirring energy here was approximately 100 W/m$^3$. (S)-3-Phenoxybenzaldehyde was actually obtained here in an optical purity of e.e. 99%, but with a yield of only 9%.

Example 8

45.6 g (0.23 mol) of m-phenoxybenzaldehyde in 12.5 ml of MTBE, 12.5 ml of toluene and 52.9 ml of dist. $H_2O$ and 12.5 ml of enzyme (Hnl from *Pichia pastoris*, 5.2 kU/ml) were charged into an inertized 100 ml Schmizo apparatus with baffles, perfusor pump, condenser, thermostat and KPG stirrer (3 cm) and the reaction mixture thus obtained was maintained at a temperature of about 20° C.

The reaction mixture was stirred at 950 rpm (3.2 kW/m$^3$ stirring energy) to produce an emulsion.

Subsequently, after an emulsion had been obtained, 12.6 ml of hydrocyanic acid (released from NaCN using $H_2SO_4$) were continuously metered in over the course of 60 min.

The emulsion was maintained for 2.5 h by intensive stirring (950 rpm). The course of the reaction was monitored by means of IP checking via the decrease in the aldehyde content.

| Reaction time | Extinction | Aldehyde content |
| --- | --- | --- |
| end of dropwise addition (1 h) | 0.978 | >30% |
| 1.5 h | 0.396 | 10.3% |
| 2 h | 0.213 | 5.6% |
| 2.5 h | 0.136 | 3.1% |

To work up the reaction solution, a further 25 ml of MTBE and 25 ml of toluene were added and it was stirred for 20 min.

The reaction mixture was allowed to stand overnight at room temperature.

An IP check after the standing time of 15 h showed an aldehyde content of 1.8%.

The reaction solution was then centrifuged once for 30 min at 3000 rpm, and the upper organic phase was aspirated and transferred to a 250 ml round-bottomed flask (org. phase 1:83.55 g). The aqueous phase was returned to the reactor, a further 25 ml of MTBE and 25 ml of toluene were added and it was stirred at 900 rpm for 20 min. The mixture was then centrifuged for 30 min.

SCMB remained as a residue in the combined organic phases.

(e.e. 98%, conversion: 92%)

Example 9

(S)-4-Fluoro-3-phenoxybenzaldehyde cyanohydrin

Analogously to Ex. 8, 10.8 g (0.05 mol) of 4-fluoro-3-phenoxybenzaldehyde in 40 ml of MTBE and 20 ml of $H_2O$ with 15 ml of enzyme (Hnl from *Pichia pastoris*, 5.2 kU/ml) were reacted at 10–15° C. with 8 ml of HCN (released from NaCN by means of $H_2SO_4$). The hydrocyanic acid was continuously metered in over the course of 30 min. The stirrer speed, which was adjusted to obtain an emulsion, was 950 rpm.

| Reaction time end of metering | Aldehyde content still no reaction |
| --- | --- |
| 1 h | >50% |
| 4 h | >30% |

After 4 h, the stirrer speed was reduced to 500 rpm and the reaction mixture was stirred at 12–15° C. for 15 h. After a total of 20 h, the aldehyde content was >5.0%. The reaction solution was drained into a measuring cylinder (yield 68.72 g) and then centrifuged once for 20 min at 3000 rpm. The organic phase was withdrawn (org. phase 1), and the aqueous phase was transferred again to the reactor, treated with 20 ml of MTBE and stirred at 900 rpm for 20 min. It was then centrifuged for 20 min again, and the organic phase was withdrawn and combined with org. phase 1.

The combined organic phases were then concentrated in a rotary evaporator.

Yield: 11.45 g of (S)-4-fluoro-3-phenoxybenzaldehyde cyanohydrin (Theory: 12.11 g) 94.55%, e.e.: 95.43%.

Example 10

(S)-3,4-Difluorobenzaldehyde cyanohydrin

Analogously to Example 8, 8.2 g (0.05 mol) of 3,4-difluorobenzaldehyde in 40 ml of MTBE and 20 ml of $H_2O$ and 15 ml of enzyme (Hnl from *Pichia pastoris*, 5.2 kU/ml) were reacted at 10–15° C. with 9 ml of hydrocyanic acid (released from NaCN).

The stirrer speed was again 950 rpm.

This time the hydrocyanic acid was added in one portion. The course of the reaction was monitored by means of IP checking.

After a reaction time of 3.5 h, aldehyde was barely detectable and after 4.5 h no further change in the aldehyde content could be detected.

The reaction solution (62.5 g) was worked up analogously to Example 9.

Yield: 8.25 g (97.74%) of (S)-3,4-difluorobenzaldehyde cyanohydrin (Theory 8.44 g) e.e.: 95.61%

Example 11

8 mmol of 3-methyl-2-butanone (860 µl) were dissolved in 2.4 ml of methyl t-butyl ether and cooled to 0° C. After addition of 750 IU of aqueous enzyme solution (Hnl from *Pichia pastoris*) (the ratio org. phase/aq. phase was 0.75:1.0), which was adjusted to pH=4.0 using citric acid, the reaction vessel was sealed pressure-tight and stirred such that an emulsion resulted. 40 mmol (1.52 ml) of hydrocyanic acid were added at 0° C. and stirring was then continued. The course of the reaction was monitored by IR spectroscopy by the decrease in the C=O band (1720 cm$^{-1}$). The 3-methyl-2-butanone was completely reacted after 2 minutes.

The phases of the reaction solution were separated, the aqueous phase was treated several times with MTBE and the MTBE solutions thus obtained were combined. The organic phase was dried over anhydrous sodium sulfate and the solvent was distilled off at 40° C. and 20 mbar. (S)-2-Hydroxy-2,3-dimethylbutanenitrile remained as a residue.

e.e.=98% (determined by gas chromatography)

The conversion was 99%.

Example 12

1250 µl of 4-methyl-2-pentanone (10 mmol) were dissolved in 3 ml of methyl t-butyl ether with stirring and cooled to 0° C. 3.9 ml (585 IU/mmol) of aqueous enzyme solution (Hnl from *Pichia pastoris*) were added. The enzyme solution had been adjusted to pH=4.5 beforehand using citric acid. The mixture was stirred for 5–10 minutes. After formation of an emulsion, 50 mmol (1.9 ml) of anhydrous hydrocyanic acid were added rapidly in one portion, the reaction vessel was sealed pressure-tight and the mixture was stirred at 0° C. for 5 minutes. The phases of the reaction solution were then separated, the aqueous phase was treated several times with methyl t-butyl ether and the MTBE solutions thus obtained were combined. The organic phase was dried over anhydrous sodium sulfate and the solvent was removed under reduced pressure.

(S)-2-Hydroxy-2,4-dimethylpentanenitrile remained as a residue.

Gas-chromatographic analysis showed an enantiomer excess of >99% and IR spectroscopy showed a conversion of 86%.

Example 13

4.6 mmol of 2-pentanone (493 μl) were dissolved in 2.4 ml of methyl t-butyl ether at 0° C. with stirring. 3.2 ml of enzyme solution (Hnl from *Pichia pastoris*, 1050 IU/mmol) were adjusted to pH=4.0 using citric acid and added only then. After this, the mixture was stirred for 5 to 10 minutes and 25 mmol (973 μl) of anhydrous hydrocyanic acid were added to the resulting emulsion.

The reaction vessel was sealed pressure-tight and stirred at 0° C. for 5 minutes (1000 rpm). The course of the reaction was monitored with the aid of IR spectroscopy by the decrease in the C=O band (1720 cm$^{-1}$). According to IR spectroscopy, the conversion was complete after this time. The phases of the reaction solution were separated from one another, the aqueous phase was treated several times with MTBE and the MTBE solutions thus obtained were combined and added to the reaction solution. The organic phase was dried over anhydrous sodium sulfate and the solvent was distilled off at 40° C. and 20 mbar.

(S)-2-Hydroxy-2-methylpentanenitrile remained as a residue.

e.e.=74% (determined by gas chromatography)

Example 14

1210 μl of 2-hexanone (10 mmol) were dissolved in 4 ml of methyl t-butyl ether with stirring and cooled to 0° C. After addition of 3.9 ml of aqueous enzyme solution of pH=4.0 (Hnl from *Pichia pastoris*, 585 IU/mmol), the reaction vessel was sealed pressure-tight and the mixture was stirred until the formation of an emulsion.

50 mmol (1.9 ml) of anhydrous hydrocyanic acid were rapidly added in one portion and the mixture was then stirred at 0° C. for 5 minutes. The reaction phases were separated from one another, the aqueous phase was treated several times with methyl t-butyl ether and the combined MTBE solutions were dried over anhydrous sodium sulfate and the solvent was removed under reduced pressure.

(S)-2-Hydroxy-2-methylhexanenitrile remained as a residue.

Gas-chromatographic analysis showed an enantiomer excess of 98.5% and a conversion of 58.5%.

Example 15

5 mmol of acetophenone (580 μl) were dissolved in 1.9 ml of methyl t-butyl ether and cooled to 0° C. 2.5 ml of enzyme solution (Hnl from *Pichia pastoris*, 750 IU/mmol) were adjusted to pH=3.75 using citric acid and added to the reaction mixture. It was then stirred for 5 to 10 minutes. 25 mmol (973 μl) of anhydrous hydrocyanic acid were added to the resulting emulsion. The reaction vessel was then sealed pressure-tight and stirred at 0° C. for 5 minutes. The course of the reaction was monitored by IR spectroscopy. The phases of the reaction solution were separated. The aqueous phase was treated several times with methyl t-butyl ether and the MTBE solutions were combined. The organic phase was dried over anhydrous sodium sulfate and the solvent was removed under reduced pressure.

(S)-2-Hydroxy-2-methylphenylacetonitrile remained as a residue.

e.e.=99%

IR spectroscopy showed a conversion of 38%.

Example 16

580 μl of acetophenone (5 mmol) were dissolved in 1.9 ml of diisopropyl ether with stirring and cooled to 0° C. 2.5 ml (750 IU/mmol) of aqueous enzyme solution having (Hnl from Pichia pastoris) were added, the enzyme solution having previously being adjusted to pH =5.0 using citric acid. The mixture was stirred for 5–10 minutes and, after formation of an emulsion, 25 mmol (0.95 ml) of anhydrous hydrocyanic acid were rapidly added in one portion. The reaction vessel was sealed pressure-tight and the reaction solution was stirred at 0° C. for a further 5 minutes. The phases of the reaction solution were separated, the aqueous phase was treated several times with methyl t-butyl ether and the MTBE solutions thus obtained were combined. The organic phase was dried over anhydrous sodium sulfate and the solvent was removed under reduced pressure.

2-Hydroxy-2-methylphenylacetonitrile remained as a residue.

Gas-chromatographic analysis showed an enantiomer excess of 99% and IR spectroscopy showed a conversion of 40%.

What is claimed is:

1. A process for the preparation of the (S)-enantiomers of optically active cyanohydrins by reaction of an aldehyde or of a ketone with a cyanide group donor in the presence of a native or of a recombinant (S)-hydroxynitrile lyase, which comprises stirring a reaction mixture of a) an aldehyde or ketone dissolved in an organic, water-immiscible or slightly miscible diluent, b) an aqueous (S)-hydroxynitrile lyase solution and c) a cyanide group donor in such a way that an emulsion is formed, which is maintained up to the end of the enzymatic reaction by stirring and after the enzymatic reaction is complete, then breaking the emulsion and isolating the corresponding (S)-cyanohydrin from the reaction mixture.

2. The process as claimed in claim 1, wherein an aliphatic, aromatic or heteroaromatic aldehyde or an unsymmetrical ketone is reacted.

3. The process as claimed in claim 1, wherein the cyanide group donor added is hydrocyanic acid.

4. The process as claimed in claim 1, wherein the hydroxynitrile lyase employed is a native (S)-hydroxynitrile lyase from *Manihot esculenta* or *Hevea brasiliensis* or a recombinant (S)-hydroxynitrile lyase derived therefrom, prepared from *Pichia pastoris* or *Saccharomyces cerevisiae*.

5. The process as claimed in claim 1, wherein the diluents used are water-immiscible or slightly miscible aliphatic or aromatic hydrocarbons which are optionally halogenated, alcohols, ethers or esters or mixtures.

6. The process as claimed in claim 1, wherein the diluent used is methyl tert-butyl ether, diisopropyl ether, dibutyl ether, ethyl acetate or a mixture of methyl tert-butyl ether and toluene.

7. The process as claimed in claim 1, wherein the reaction temperature is 0° C. to 30° C.

8. The process as claimed in claim 1, wherein stirring is carried out with a stirring energy above 500 W/m$^3$.

* * * * *